US009116365B2

(12) United States Patent
Haddadi et al.

(10) Patent No.: US 9,116,365 B2
(45) Date of Patent: *Aug. 25, 2015

(54) METHOD FOR DETERMINING AT LEAST ONE GEOMETRIC/PHYSIOGNOMIC PARAMETER ASSOCIATED WITH THE MOUNTING OF AN OPHTHALMIC LENS IN A SPECTACLE FRAME WORN BY A USER

(75) Inventors: Ahmed Haddadi, Charenton-le-Pont (FR); Jean Delzers, Charenton-le-Pont (FR)

(73) Assignee: ESSILOR INTERNATIONAL (COMPAGNIE GENERALE D'OPTIQUE), Charenton le Pont (FR)

( * ) Notice: Subject to any disclaimer, the term of this patent is extended or adjusted under 35 U.S.C. 154(b) by 37 days.

This patent is subject to a terminal disclaimer.

(21) Appl. No.: 13/985,170

(22) PCT Filed: Dec. 30, 2011

(86) PCT No.: PCT/FR2011/000688
§ 371 (c)(1),
(2), (4) Date: Aug. 13, 2013

(87) PCT Pub. No.: WO2012/113995
PCT Pub. Date: Aug. 30, 2012

(65) Prior Publication Data
US 2013/0314668 A1 Nov. 28, 2013

(30) Foreign Application Priority Data
Feb. 21, 2011 (FR) ...................................... 11 00512

(51) Int. Cl.
*G02C 13/00* (2006.01)
*A61B 3/11* (2006.01)
*A61B 5/00* (2006.01)

(52) U.S. Cl.
CPC .............. *G02C 13/005* (2013.01); *A61B 3/111* (2013.01); *A61B 5/6803* (2013.01)

(58) Field of Classification Search
CPC ...... G02C 13/005; A61B 3/111; A61B 5/6803
USPC .................................................... 351/204, 245
See application file for complete search history.

(56) References Cited

U.S. PATENT DOCUMENTS 7,588,335 B2 * 9/2009 Kubitza ......................... 351/204
8,182,089 B2 * 5/2012 Sayag ............................ 351/204
(Continued)

FOREIGN PATENT DOCUMENTS

| WO | 01/84222 | 11/2001 |
| WO | 2005/071468 | 8/2005 |
| WO | 2006/029875 | 3/2006 |

(Continued)

OTHER PUBLICATIONS
International Search Report dated Mar. 27, 2012, corresponding to PCT/FR2011/000688.

*Primary Examiner* — Jordan Schwartz
(74) *Attorney, Agent, or Firm* — Young & Thompson (57) ABSTRACT

Method includes: (a) placing on a user's head an accessory including at least one brightness calibration element having at least two contrasted zones; (b) capturing an image of the user's head with the accessory thereon with a device; (c) determining the position of the image of the brightness calibration element of the accessory on the captured image; (d) determining a measured value of the brightness of one part of the image of the brightness calibration element or of the image located close to the brightness calibration element; (e) modifying a parameter for adjusting the optical image-acquisition conditions of the device as a function of the measured value to improve the contrast of the image of contrasted zones of the calibration element; (f) capturing another image with the modified parameter for adjusting the optical acquisition conditions; and (g) determining the required geometric/physiognomic mounting parameter on the basis of the other image.

18 Claims, 3 Drawing Sheets

(56) References Cited

U.S. PATENT DOCUMENTS

2009/0262302 A1* 10/2009 Chauveau et al. ............ 351/204
2012/0257162 A1* 10/2012 Encaoua et al. ............. 351/204

FOREIGN PATENT DOCUMENTS

WO  2009/024681  2/2009
WO  2010/016379  2/2010

* cited by examiner

METHOD FOR DETERMINING AT LEAST ONE GEOMETRIC/PHYSIOGNOMIC PARAMETER ASSOCIATED WITH THE MOUNTING OF AN OPHTHALMIC LENS IN A SPECTACLE FRAME WORN BY A USER

BACKGROUND OF THE INVENTION

1. Field of the Invention

The present invention relates in a general manner to a method for determining at least one geometric/physiognomic parameter associated with the mounting of an ophthalmic lens in a spectacle frame worn by a user.

2. Description of the Related Art

The manufacture of a corrective spectacle lens comprises, on the one hand, the optical design and shaping of the refractive surfaces of the lens and, on the other hand, the adaptation of the lens to the chosen frame.

The present invention relates to the measurement, on the face of the user, of geometric/physiognomic parameters taking into account the fitting configuration of the spectacles on the user's face. These parameters are likely to be used in the two steps of manufacture of a corrective lens so that the lens finally performs the corrective optical function for which it was designed and prescribed. This notably involves the inter-pupillary distance, the height of the pupils of the users eyes in relation to the lower edge of the frame, and/or the pantoscopic angle formed by the general plane of the frame or the lens in relation to the perpendicular.

In a known manner, it is possible to determine these parameters on the basis of one or more captured images of the users head.

It is also useful to determine the optical behavior of the user, for example by determining the orientation of the gaze and the head of the user when the latter follows a moving point with his eyes, for example during a movement of the head from left to right and/or from right to left. A video acquisition of a plurality of images during the movement of the head is particularly suitable for this purpose.

The determination of the aforementioned parameters entails the identification on the captured image of the image of at least one reference element disposed on the face of the user and having at least one predetermined geometric characteristic.

It is then possible to determine the looked-for geometric/physiognomic parameter by comparing the geometric characteristic of the image of the reference element and its corresponding real geometric characteristic.

However, this method can only be carried out if the identification of the reference elements on the captured image is possible.

A positioning of the user backlit in relation to the image capture device can result in the capture of an unusable image, as it is too dark to allow identification of the reference element.

Moreover, if the user's head is illuminated at least partially by daylight, the illumination of the user's head may vary, either according to the course of the sun in the sky, or, in the case of a dynamic measurement, according to the position of the user's head in relation to the light sources illuminating it. Thus, the conditions of illumination of the user's head can be variable.

The situations in which the reference elements of the user's head appear too dark to be identified precisely on a captured image are therefore multiple.

A first solution to this problem is to place the image capture device in a location where the illumination is perfectly controlled and constant. The main disadvantage of this solution is that it limits considerably the locations that are favorable for the installation of the device allowing the method to be carried out.

The optician may then be forced to place the image capture device in a sealed room. He cannot then place it in a shop window, even though that offers advantages from a commercial point of view.

A different solution is to use an image capture device comprising automatic means for adjusting the brightness of the captured image. However, these means carry out an adjustment of the mean brightness of the entire image, which does not allow a usable image to be obtained in the case of a backlit image capture, for example.

Other known image capture devices comprise means for manual brightness adjustment. The brightness setting can then be adjusted before each image capture. However, this has the disadvantage of being long and tedious for the optician. Furthermore, this cannot be implemented in the context of a continuous image acquisition in video mode.

SUMMARY OF THE INVENTION

One object of the present invention is therefore to overcome the aforementioned disadvantages of the prior art, by proposing a method for determining at least one geometric/physiognomic parameter associated with the mounting of an ophthalmic lens in a frame which can be carried out regardless of the ambient brightness conditions.

According to the invention, a method as defined in the introduction is proposed for this purpose, consisting in:

a) placing an accessory on the user's head, said accessory comprising at least one brightness calibration element including at least two contrasted zones;

b) capturing an image of the user's head on which said accessory has been placed, using an image capture device;

c) determining the position of the image of the brightness calibration element of said accessory on said image captured in step b);

d) determining a measured value of the brightness of at least one part of the image of this brightness calibration element;

e) modifying a parameter for adjusting the optical image-acquisition conditions of said image capture device as a function of this measured value in such a way as to improve the contrast of the image of the contrasted zones of the calibration element;

f) capturing another image with the modified parameter for adjusting the optical acquisition conditions; and g) determining said looked-for geometric/physiognomic mounting parameter on the basis of this other image.

Thus, an automatic adjustment of the optical image capture conditions guarantees to capture an image usable for determining the looked-for geometric/physiognomic parameter.

For this purpose, the brightness of the image is adjusted by modifying a parameter for adjusting the optical acquisition conditions as a function of the brightness of the image of a brightness calibration element on the captured image.

In one preferred embodiment of the invention, the calibration element is combined with a reference element of which the known real geometric characteristics measured on the image are used to determine the looked-for geometric/physiognomic parameter.

The brightness adjustment is then implemented in such way as to be optimized directly on the image of this reference element, guaranteeing that the image of this reference element will be identifiable on the image captured in step f) with the modified parameter for adjusting the optical acquisition conditions.

Alternatively, it can be provided that the calibration element is disposed close to the reference element used in step g): the brightness adjustment is then carried out for an area of the image very close to the reference element.

According to other advantageous and non-limiting characteristics of the invention:

- after step e), steps b) to e) are repeated while the brightness value measured in step d) is outside an interval of predetermined values, and steps f) and g) are carried out when this measured value is located inside said predetermined interval;
- the accessory furthermore comprising a reference element having at least one known geometric characteristic, in step g), at least one geometric characteristic of this reference element of the accessory is identified on the image captured in step f);
- said reference element is combined with said brightness calibration element;
- in step d), the part of the image of the brightness calibration element for which a measured value of the brightness is determined straddles said two contrasted zones;
- in step d), a measured value of the brightness of each contrasted zone of the image of this brightness calibration element is determined and the average of these two values is calculated;
- in step e),
  - the difference between the measured brightness value determined in step d) and a target brightness value is determined,
  - this difference is compared with a predetermined maximum value of this difference,
  - according to this comparison, the parameter for adjusting the optical acquisition conditions of the image capture device is modified in such a way as to make said measured value extend towards said target brightness value;
- it comprises the following steps, which are preliminary to step b):
  - pa) capturing a preliminary image of the user's head,
  - pb) determining a measured value of the mean brightness of at least one reduced zone of this preliminary image, this reduced zone being suitable for covering at least a part of the image of the users head,
  - pc) roughly adjusting the parameter for adjusting the optical acquisition conditions of the image capture device according to this measured value in such a way as to improve the contrast of the captured image of the user's head,
  - pd) using the parameter for adjusting the optical acquisition conditions obtained in step pc) to adjust the optical conditions of the image capture of step b),
- more particularly, in step pc),
  - the difference between the measured value of the brightness determined in step pb) and a target brightness value is determined,
  - this difference is compared with a predetermined maximum value of this difference,
  - according to this comparison, in step pc), the parameter for adjusting the optical acquisition conditions of the image capture device is adjusted in such a way as to make said measured value extend towards said target brightness value;
- it comprises, in step c), a step k) of detection of the groups of pixels having an isolated brightness peak smaller in size than the brightness calibration element in all directions;
- a step l) of selection of at least two groups of pixels having an isolated brightness peak detected in step k) is provided, having the highest probability of being associated with the image of two of the brightness calibration elements of the accessory, i.e. at least two groups of pixels for which the difference between:
  - a distance measured between these two groups and a reference distance, and/or
  - an angle measured between the straight line passing through these two groups and a reference direction and a reference angle, and/or
  - the brightness measured in the vicinity of these two groups and a reference brightness, and/or
  - the brightness difference between two points of predetermined relative positions in relation to each group of pixels and a reference brightness difference is reduced;
- the pairs of two groups of pixels for which the difference between a distance measured between these two groups and a reference distance, and/or an angle measured between the straight line passing through these two groups and a reference direction and a reference angle, and/or the brightness measured in the vicinity of these two groups and a reference brightness and/or the brightness difference between two points of predetermined relative position in relation to each group of pixels and a reference brightness difference is greater than a threshold value are excluded from the selection made in step l);
- the method comprises a step of resampling of the image obtained in step b) intended to reduce the total number of pixels of the image;
- said contrasted zones of the brightness calibration element comprise a dark gray zone and a light gray zone;
- each brightness calibration element comprises four alternating contrasted zones, each zone forming a right angle with a common apex with the right angles formed by the other zones;
- the accessory is fixed onto the spectacle frame of the user.

BRIEF DESCRIPTION OF THE DRAWING FIGURES

The description which follows, with reference to the appended drawings, which is given by way of a non-limiting example, will make it clear what the invention consists of and how it can be implemented.

In the attached drawings.

DETAILED DESCRIPTION OF THE INVENTION

Figure 1:
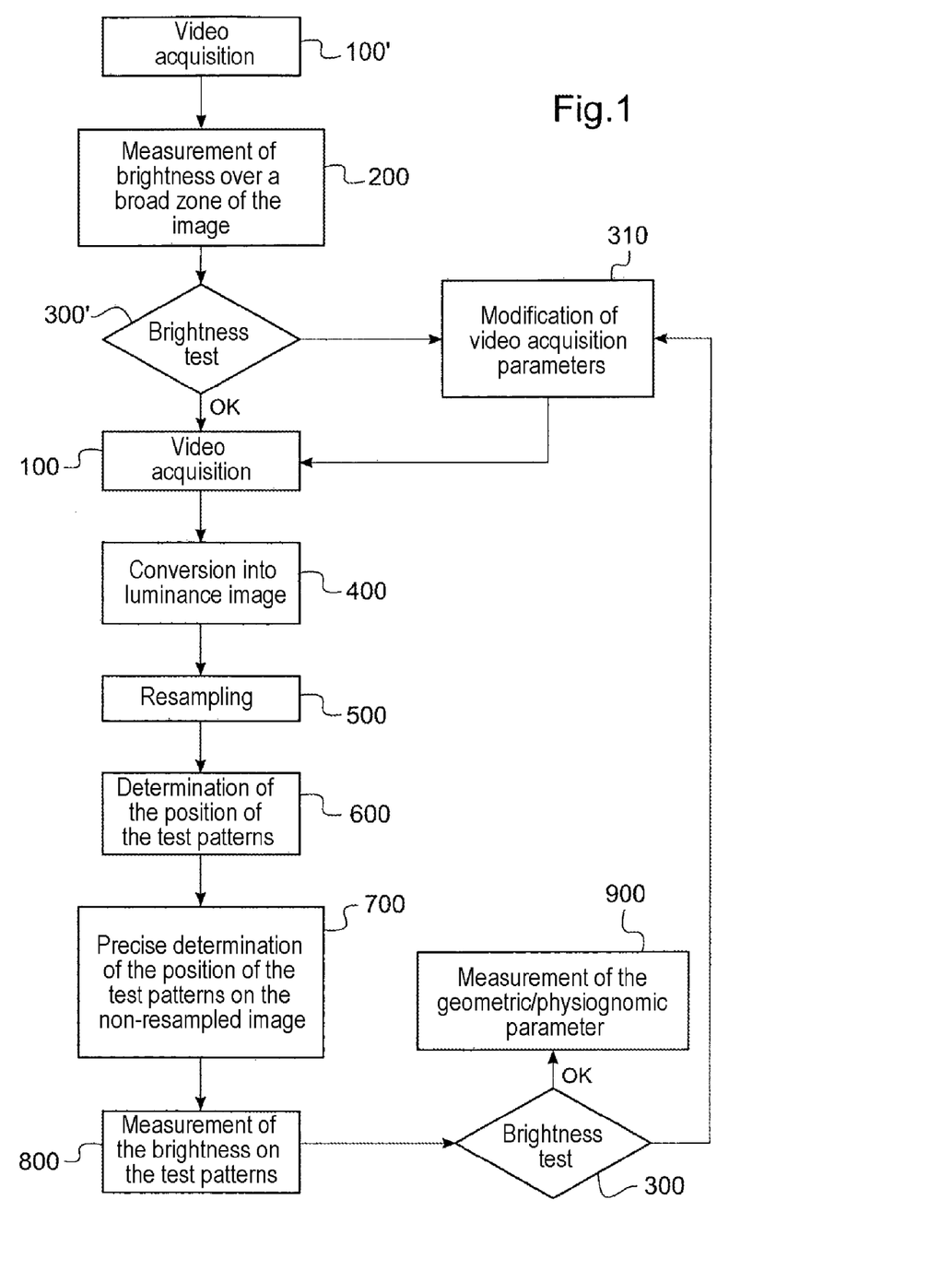
FIG. 1 is a schematic diagram of the steps of one possible embodiment of the invention.

FIG. 1 shows the steps of one possible embodiment of the method according to the invention.

The purpose of carrying out this method is to determine at least one geometric/physiognomic parameter associated with the mounting of an ophthalmic lens in a spectacle frame worn by a user, such as, for example, the interpupillary distance, the height of the pupils of the user's eyes in relation to the lower edge of the frame, and/or the pantoscopic angle formed by the general plane of the frame or the lens in relation to the perpendicular.

The method comprises the following steps, which are described below in more detail:

a) placing an accessory on the user's head comprising at least one brightness calibration element including at least two contrasted zones;

b) capturing an image of the user's head on which said accessory has been placed, using an image capture device;

c) determining the position of the image of the brightness calibration element of said accessory on said image captured in step b);

d) determining a measured value of the brightness of at least one part of the image of this brightness calibration element or of at least one part of the image situated near this brightness calibration element;

e) modifying a parameter for adjusting the optical image-acquisition conditions of said image capture device as a function of this measured value in such a way as to improve the contrast of the image of the contrasted zones of the calibration element;

f) capturing another image with the modified parameter for adjusting the optical acquisition conditions; and g) determining said looked-for geometric/physiognomic mounting parameter on the basis of said other image.

Step a)

Figure 3:
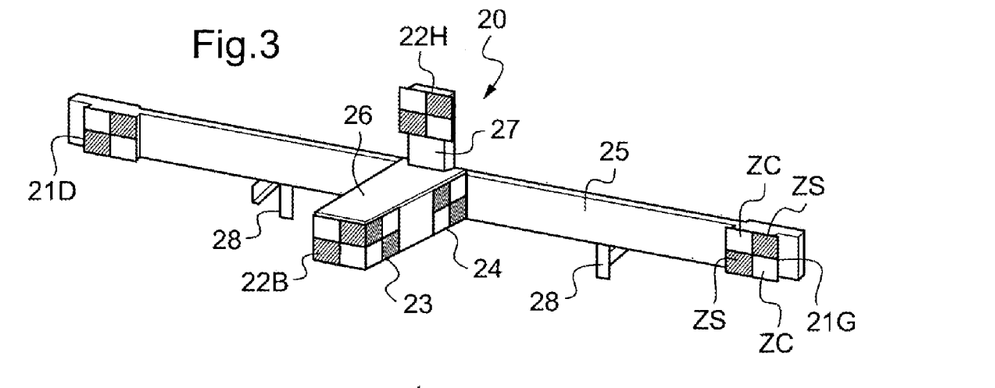
FIG. 3 is a schematic top view of an accessory comprising calibration elements to carry out the method according to the invention.
Figure 6:
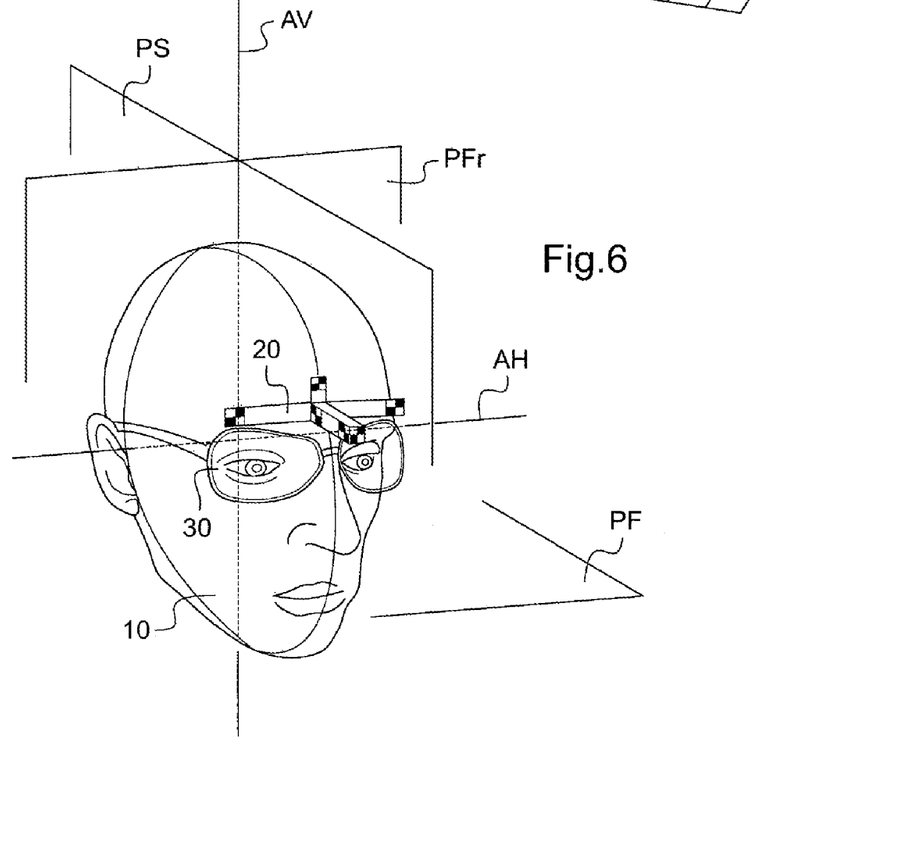
FIG. 6 is a schematic view of the head of the user equipped with the spectacle frame and the accessory.

An accessory 20, an example of which is shown in FIG. 3, is placed on the user's head 10 (FIG. 6).

The accessory 20 shown in FIG. 3 is intended here to be mounted on the spectacle frame 30 of the user. It comprises (FIG. 3) a main bar 25 suitable for being disposed above the spectacle frame, in a mean plane of the circles of this frame and in such a way as to extend more or less parallel to a straight line connecting the pupils of the users eyes.

For this purpose, the accessory 20 has mounting means on the frame 30, present here in the form of clips 28 extending from the main bar 25.

Two clips 28 are provided here, each suitable for being hooked onto one of the circles of the frame 30.

This accessory 20 also comprises a projection 26 extending perpendicular to the main bar 25, in a plane more or less perpendicular to the mean plane of the circles of the frame when the accessory 20 is fixed onto this frame 30, and a projecting element 27 extending perpendicular to the main bar 25 and to the projection 26, in the mean plane of the frame 30 when the accessory 20 is fixed onto this frame.

As shown in FIG. 6, a Frankfurt plane PF is defined for the users head, passing through the lower orbital points OR and the porion PO of the user, the porion being the highest point on the skull of the ear canal, corresponding to the tragion of the ear. This Frankfurt plane is more or less horizontal when the user adopts a natural posture.

This is the case, for example, when the user is in a seated or standing position in which his head 10 is straight and he is looking straight in front of him, into the distance, i.e. preferably at the horizon. The axis of the users gaze is then horizontal.

It is also said that the user adopts an orthostatic position, or a position in which he exerts a minimum of effort.

A sagittal plane PS is defined as being the plane perpendicular to the Frankfurt plane passing through the perpendicular bisector of the two eyes. The perpendicular bisector of the eyes is the axis passing through the middle of the segment defined by the centers of rotation CROG, CROD of the two eyes and parallel to the Frankfurt plane PF.

A frontal plane PFr of the head is also defined as being a plane perpendicular to the Frankfurt plane and parallel to the straight line connecting the two eyes and passing through the top of the head.

Under these conditions, a vertical axis AV of the head 10 is defined as the intersection of the frontal and sagittal planes and a horizontal axis AH of the head is defined as the intersection of the Frankfurt and frontal planes. This horizontal axis AH is therefore an axis perpendicular to the sagittal plane PS of the user's head.

A front image then corresponds to an image for which the image capture plane of the image capture device forms an angle of between +20 and −20 degrees with the frontal plane PFr of the user's head around the vertical axis AV of the users head.

A profile image then corresponds to an image for which the image capture plane of the image capture device forms an angle of between +10 and −10 degrees with the sagittal plane PS of the user's head around the vertical axis AV of the user's head, corresponding to an angle between the frontal plane PFr and the image capture plane of between 80 and 100 degrees.

The accessory 20 comprises at least one brightness calibration element 21D, 21G, 22H, 22B, 23, 24, comprising at least two contrasted zones ZS, ZC.

Here, the accessory 20 comprises eight calibration elements 21D, 21G, 22H, 22B, 23, 24. Two calibration elements 21D, 21G are disposed at the ends of the main bar 25, and are oriented in such way as to be visible at least on a front image of the user, when the accessory 20 is fixed onto the frame of the user.

One calibration element 22H is disposed on the projecting element 27, and another calibration element 22B is disposed at the end of the projection 26, in such a way that these two calibration elements 22H, 22B are visible at least on a front image of the user. Moreover, these two calibration elements 22H, 22B are disposed in such a way that, in a front view of the accessory, they are located one below the other.

The calibration elements 21D, 21G, 22H, 22B visible at least on the images captured from the front are referred to below as front calibration elements.

Finally, the lateral sides of the projection also each carry two calibration elements 23, 24 which are visible at least on the profile images of the user and are referred to below as profile calibration elements.

In practice, the calibration elements 21G, 21D, 22H, 22B, 23, 24 are visible over a wide range of relative inclinations between the user's head and the image capture device.

Here, each calibration element comprises four contrasted zones ZS, ZC. These contrasted zones are disposed alternately, each zone forming a right angle with a common apex with the right angles formed by the other zones. Said common apex of the light and dark zones forms the center of the calibration element.

These calibration elements are also referred to as "test patterns", as is the case, for example, in FIG. 1.

Figure 4A:
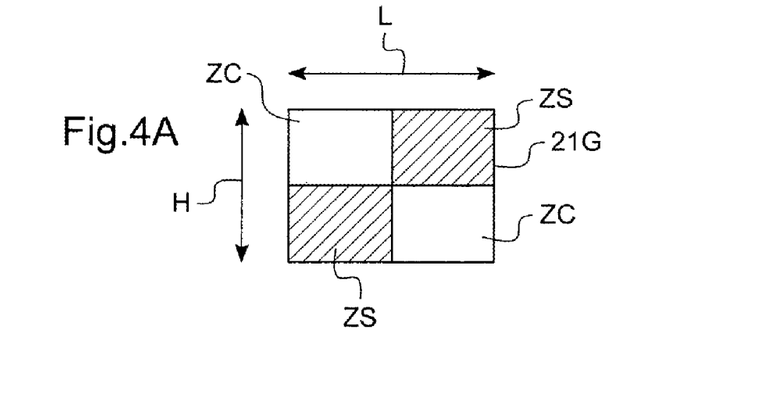
FIG. 4A is a schematic front view of a calibration element of the accessory shown in FIG. 3, visible at least in a front view of this accessory.

In practice, as shown in more detail in FIG. 4A for the calibration element 21G, each front calibration element 21D, 21G, 22H, 22B is present here in the form of a rectangle with a length L of between 8 and 11 millimeters and a height H of between 5 and 8 millimeters.

Alternatively, said calibration elements may have any other shape, notably a square or circular shape.

This rectangle is divided into four smaller rectangles of equal dimensions. The smaller rectangles have, two-by-two diagonally, identical luminance or colors, and have, two-by-two with their neighbor, different luminance or colors.

Figures 4B, 5:
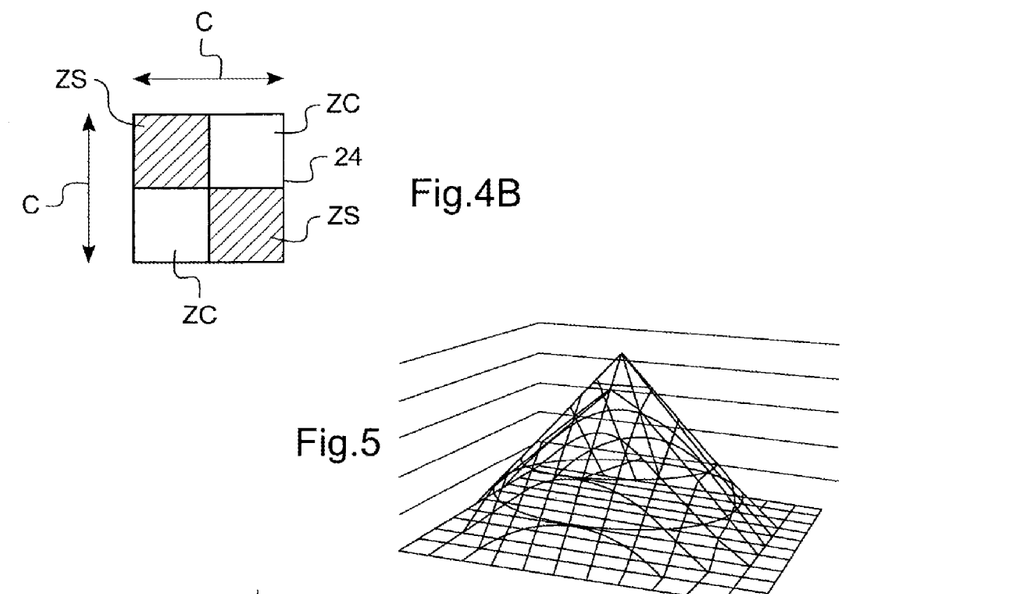
FIG. 4B is a schematic front view of a calibration element of the accessory shown in FIG. 3, visible at least in a profile view of this accessory.
FIG. 5 is a schematic view of the coefficients of a reinforcement matrix used in the processing of the captured image, as explained below.

As shown in more detail in FIG. 6B for the profile reference element 23, the profile reference elements 23, 24 preferably have a square shape with a side with a length C equal to 6 millimeters. This square is divided into four smaller squares of equal dimensions. The smaller squares have, two-by-two diagonally, identical luminance or colors, and have, two-by-two with their neighbor, different luminance or colors.

In the example shown in FIGS. 3, 4A and 4B, the calibration elements comprise zones contrasted in luminance: these are dark zones and light zones of the same color. More precisely, the contrasted zones ZS, ZC here are non-saturated light gray and dark gray zones. In this case, the calibration elements allow a luminance calibration, and brightness is understood to mean a luminance value.

The luminance distribution is furthermore inverted between the front and profile calibration elements (FIGS. 4A and 4B).

In a color-coding of the Red Green Blue type, the light gray zones correspond, for example, to three components with an intensity equal to 225 and the dark gray zones correspond to three components with an intensity equal to 51.

The contrasted zones ZS, ZC are preferably not saturated, i.e. they are not black and white.

Alternatively, said contrasted zones of the calibration element comprise zones of different colors. These are then zones contrasted in chrominance. For example, a calibration element totally similar to the element previously described can be envisaged, in which alternate red and green zones are provided.

In this case, the calibration element allows a chrominance calibration, and brightness is understood to mean a chrominance value.

These zones can then have identical luminance, or can also be contrasted in luminance.

The rectangular shape of the calibration element, with a greater length according to the axis of the main bar 25 of the accessory 20, enables effective detection of this calibration element, even if the user moves his head 10 (see FIG. 5), notably according to a lateral movement from left to right or from right to left around the vertical axis AV.

For example, with a calibration element measuring 10 millimeters in length and 7 millimeters in height, if the user's head turns through an angle of 45 degrees around its vertical axis AV in relation to the orientation of the head when the frontal plane of the latter is parallel with the image capture plane of the image capture device, the image of the calibration element on the image of the user's head captured by the image capture device then measures 7 millimeters in length by 7 millimeters in height, ensuring easy identification of the image of this calibration element.

In the example described here, the accessory 20 comprises calibration elements 21D, 21G, 22H, 22B which are visible at least on the images captured from the front of the users head and calibration elements 23, 24 visible at least on the images captured in profile.

In practice, it is advantageously possible to easily identify at least one front calibration element of the accessory over a wide range of orientation of the head 10 in relation to the image capture device, for example over an inclination range of the frontal plane PFr of the head in relation to the image capture plane of between −45 and +45 degrees around the vertical axis AV of the user's head.

This inclination range is as great as the length of the calibration elements in the direction of the main bar 25 of the accessory. It is therefore possible to adjust the dimensions of the calibration elements according to the relative range of inclinations of the frontal plane PFr of the head and the image capture plane provided during the capture of a given series of images.

The front and profile calibration elements have different distributions of contrasted zones in such a way as to be easily differentiated from one another.

In the example described here, the brightness adjustment is carried out using the front calibration elements only.

Alternatively, it can be envisaged to perform this brightness adjustment in relation to the front and profile calibration elements.

The accessory 20 also comprises position reference elements having shape and color characteristics which make their position on the image easy to determine and of which a real geometric characteristic is predetermined and known.

This real geometric characteristic is compared to the corresponding geometric characteristic of the image of this reference element to deduce from it a scale factor, and/or an angle of orientation of the head around its vertical axis AV, and/or an angle of orientation of the users head around the horizontal axis AH.

The position reference elements are advantageously combined here with the calibration elements 21D, 21G, 22H, 22B, 23, 24. The alternation of the light zones ZC and dark zones ZS in fact creates a test pattern, the position of which can easily be detected, as explained in more detail below, and of which the geometric characteristics are known and can be used to determine the looked-for geometric/physiognomic parameter.

Alternatively, the accessory can be envisaged to comprise at least one position reference element distinct from the brightness calibration elements.

For example, the position reference element may be a green test pattern disposed close to one of the calibration elements. The relative position of the calibration element in relation to this reference element is then predetermined.

Step b)

An image of the user's head on which said accessory has been placed is captured, using an image capture device.

This image capture device may be any known image capture device, notably a digital image capture device.

If the image capture device is a non-digital optical device, the captured image is converted into a digital image before any other step of processing of this image.

The image capture device is preferably a video image capture device capturing between 1 and 30 images per second. Taking into account the aspects associated with image processing, notably the computing time required to process the images, preferably between 5 and 20 images per second are captured and processed.

The image capture device used captures, for example, 15 images per second which are processed by the method described here.

Not all of the captured images are used to determine the looked-for geometric/physiognomic parameter, but some of them allow the adjustments of the image capture device to be fine-tuned as explained below, in such a way as to improve the brightness of the subsequently captured images of the reference elements of the accessory 20, in such a way as to ensure their precise identification.

In practice, a series of images is therefore captured at more or less regular time intervals (block 100 in FIG. 1). The image capture parameters of the capture device are modified according to the steps described below as the images are captured and processed.

Here, the captured images are, for example, black and white images in which each pixel has a given luminance.

Figure 2:
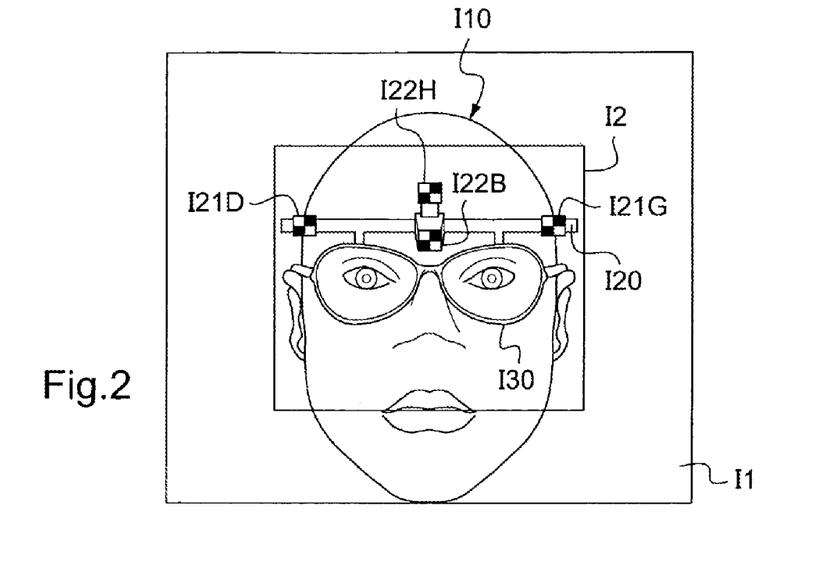
FIG. 2 is a schematic view of an image captured by the image capture device.

An image I1 of this type is, for example, shown in FIG. 2. In this FIG. 2, the image I1 is a front image of the head 10 of the user. It comprises the image of the head I10, the image of the frame I30, and the image of the accessory I20 on which the images of the calibration elements I21D, I21G, I22H, I22B can be identified. The images I23, I24 of the profile calibration elements are not identifiable on this front image.

An image of the user's head is captured in a general manner having an orientation in relation to the image capture device such that at least one of the previously described calibration elements is visible on the image. This condition is verified over a very wide range of relative inclinations between the frontal plane PFr of the user's head and the image capture plane, as previously explained.

This image may, in particular, be a front image of the user's head, or an image corresponding to a relative inclination of the frontal plane PFr of the head in relation to the image capture plane of between −45 and +45 degrees around the vertical axis AV of the user's head.

Alternatively, it is possible to capture a profile image of the user.

Alternatively, it can also be envisaged to capture a color image, i.e. in which each pixel contains luminance and chrominance information, and convert this color image into a grey tone image, which is shown on the block 400 in FIG. 1.

To do this, the image captured in coding (R, G, B) comprising red R, green G, and blue B components is transformed in a known manner into coordinates (Y,U,V) comprising luminance Y and chrominance U,V. The luminance of each pixel is obtained according to the following formula:

$$Y = 0.299*R + 0.587*G + 0.114*B.$$

Step c)

The position of the image of at least one of the brightness calibration elements 21D, 21G, 22H, 22B, 23, 24 of said accessory 20 is determined on the image captured in step b), as shown on the block 600 in FIG. 1.

To do this, a step of resampling of the image obtained in step b) is preferably first carried out in practice, which is intended to reduce the total number of pixels of the image (block 500 in FIG. 1).

The subsequent image processing steps described below are then faster, since the computing times are reduced with the reduction in the number of pixels of the image.

The resampling coefficient is, for example, between 1.5 and 3. It is, for example, equal to 2.

Alternatively, it is of course possible to use the non-resampled image captured in step b).

To determine the position of the image of each calibration element on the image, the position of the images of these calibration elements is determined here directly through processing of the captured image.

Alternatively, as mentioned above, the position of the images of the position reference elements of the accessory could be determined and the position of the calibration elements could be deduced from this.

In step c), a step i) of convolution of at least one part of the image captured in step b) is carried out by means of a detection matrix reproducing the expected brightness distribution of the image of one of the calibration elements.

This brightness distribution may be a luminance or chrominance distribution according to the type of calibration element used, as explained above.

Here, given the arrangement of the dark ZS and light ZC zones of each calibration element 21D, 21G, 22H, 22B in the convolution step i), said detection matrix has the following form:

$$\begin{vmatrix} m & -m \\ -m & m \end{vmatrix}$$

Each element m of the detection matrix is a sub-matrix comprising a number of rows and a number of columns such that the convolution matrix has dimensions which are less than or equal to the corresponding expected dimensions in pixels of the image of one of the reference elements, taking into account an envisaged maximum angle between the frontal plane of the user's head and the image capture plane.

In fact, as previously mentioned, taking into account the rotation of the user's head around its vertical axis AH, the image of the calibration element I21D, I21G, I22H, I22B, I23, I24 (FIG. 2) does not necessarily have a rectangular shape.

For example, if the calibration element in reality measures 10 millimeters in length by 6 millimeters in height, its image extends over an image captured in a front view over 20 pixels in length and 12 pixels in height.

On an image captured when the frontal plane PFr of the user's head is, for example, turned through 45 degrees in relation to the image capture plane PCI around the vertical axis AV, the image of the calibration element extends over 12 pixels in length and 12 pixels in height.

Following the resampling, the image of the calibration element on the image captured at 45 degrees then extends over 6 pixels in length and 6 pixels in height.

Each dark zone ZS and each light zone ZC of the calibration element therefore extends over 3 pixels in length and 3 pixels in height.

Each element m of the detection matrix then comprises, for example, 3 columns and 3 rows so that the size of the detection matrix remains less than or equal to the size of the image, regardless of the orientation of the user's head in relation to the image capture plane.

In the example described here, the brightness of each dark or light zone is uniform, and the coefficients of each element m of the detection matrix are then preferably all equal.

Moreover, the sum of the positive coefficients of the detection matrix is preferably equal to 1 in order to avoid saturation phenomena during the convolution.

In the example presented here, the matrix m then has the following form:

$$m = 1/18 * \begin{vmatrix} 1 & 1 & 1 \\ 1 & 1 & 1 \\ 1 & 1 & 1 \end{vmatrix}$$

The convolution of the image captured in step b) by the detection matrix is, for example, carried out for the totality of the image. This allows the image of each calibration element to be identified without a priori knowledge of the position of the latter in the image, which is notably the case during the convolution of the first image of a series of images.

In practice, the two profile reference elements 23, 24 are not identified here during the described image processing as they have a luminance distribution which differs from that of the front calibration elements 21D, 21G, 22H, 22B, as shown in FIGS. 3, 4A and 4B. A selective detection of the front and profile calibration elements can therefore be carried out.

In practice, the light and dark zones are inverted here on the profile reference elements. The detection matrix used to determine the position of the front reference elements is not therefore suitable for determining the profile reference elements.

It could also be envisaged to carry out a step of approximate estimation of the position of the calibration elements before this convolution step. To do this, the image of the pupils of the users eyes is identified on the captured image and an area of the image in which each calibration element has a high probability of being located is deduced from this, knowing through calibration the approximate position of the reference elements in relation to the user's pupils.

It is also possible to carry out a tracking of the position of the calibration elements: on the basis of the position on a given image of the head of the user of the calibration element, his approximate position can be estimated in the following image, for example according to the time interval between two image captures and the average speed of movement of the user's head.

In practice, the speed of movement of the head is determined through comparison of the two images preceding the performed image capture.

On the following image, the calibration element is thus located in an area centered around a zone corresponding to the position of the image of the calibration element on the preceding image, the radius of which is equal to the maximum estimated movement of the calibration element between two image captures.

Only a part of the following image, located in the previously determined area, is then convoluted by the detection matrix. The calculation is thus faster.

In the example described, implementing a luminance calibration element, the area of the image convoluted by the detection matrix comprises groups of pixels belonging to the calibration elements and other groups of pixels which do not belong to the calibration elements.

It is then possible to carry out a step j) of reinforcement of the contrast of the image convoluted in step i), during which at least one part of the captured image is convoluted by a reinforcement matrix, the dimensions of which are less than or equal to the corresponding dimensions in pixels of the image of a calibration element, and of which the coefficients increase from the edges toward the center of the reinforcement matrix.

The distribution of the coefficients of such a matrix is shown schematically in FIG. 5, which shows the amplitude of the coefficients according to their positions in the matrix.

The size of this reinforcement matrix depends on the size of the image of the calibration element, and therefore on the resampling coefficient.

The convolution of the image obtained in step i) by this reinforcement matrix enables an increase in the luminance of the pixels located in the zones of which the luminance follows the expected distribution for the image of each calibration element.

The determination of the position of the calibration elements is thus more precise.

A step k) of searching for the isolated maxima is then carried out on the image obtained in step j), or on the image obtained in step i) if the convolution by the contrast reinforcement matrix is not carried out.

More precisely, in step k), groups of pixels having an isolated brightness peak and having a size less than the size of the brightness calibration element in all directions are detected.

To do this, the pixels of which the brightness is greater than a predetermined brightness threshold value are referenced on the image obtained in step i) or j).

This may of course involve a luminance or chrominance threshold value according to the type of calibration element used.

A filling algorithm of an isolation matrix centered on each referenced pixel is then used. This algorithm fills the matrix with brightness values of the pixels adjacent to said referenced pixel if this brightness is greater than said threshold value.

The size of the isolation matrix is chosen according to the size of the looked-for image of the calibration element.

If the isolation matrix remains empty along its edges, this means that the group of pixels located around the referenced pixel corresponds to an isolated maximum.

A first selection, for example, is carried out among all the groups of pixels identified in step k) by retaining only the ten groups of which the brightness is the greatest.

A step l) of selection of at least two groups of pixels having an isolated brightness peak detected in step k) and having the highest probability of being associated with the image of two of the brightness calibration elements of the accessory is then carried out, i.e. at least two groups of pixels for which the difference between     a distance measured between these two groups and a reference distance, and/or     an angle measured between the straight line passing through these two groups and a reference direction and a reference angle, and/or     the brightness measured in the vicinity of these two groups and a reference brightness, and/or     the brightness difference between two points of predetermined relative positions in relation to each group of pixels and a reference brightness difference is reduced.

To do this, all of the pairs of groups of pixels present on the image according to a given direction are determined, for example by considering a first group of pixels and each other group of pixels located to the left or to the right of this first group, or above or below this first group.

A global rating is awarded to each pair of groups of pixels in such a way as to quantify their resemblance to the image of a given pair of calibration elements of the accessory.

By way of example, the two calibration elements 21D, 21G, for example, disposed at each end of the main bar 25 of the accessory 20 are considered.

A similar processing can obviously be carried out for the calibration elements 22H, 22B disposed one below the other on the projecting element and the projection of the accessory 20, or for the two calibration elements disposed on each side of the projection.

The global rating awarded to each pair is determined according to the comparison of geometric and brightness characteristics of the groups of pixels with the expected characteristics of the image of the pair of calibration elements considered.

For example, the distance measured on the image between the two groups of this pair and the expected distance between the images of the two calibration elements of the pair considered are compared, and a first intermediate rating is awarded to the pairs considered, which is larger, the smaller the difference between these two distances. The expected distance between the images of the two calibration elements is determined according to a scale factor taking into account notably the resampling of the image.

A comparison is also made between the angle measured on the image between the straight line passing through these two groups and a direction representing, for example, the image of a horizontal straight line and the expected angle between the straight line connecting the images of the two calibration elements and the image of a horizontal plane. A second intermediate rating, which is larger the smaller the difference between these two angles, is then awarded to the pair considered.

A comparison is also made between the brightness measured in the vicinity of these two groups and a reference brightness determined according to the preceding image captures.

When a series of images is captured, it can be supposed that the brightness values measured on two successive images will be close to one another. Thus, a third intermediate rating, which is larger the smaller the aforementioned brightness difference, is awarded to the pair considered.

Finally, a comparison can be made here, for example, for each group of pixels of said pair, between a reference brightness difference and the brightness difference between two points of relative positions chosen so that they are located in two adjacent faces and/or two diagonally opposite faces of the image of the reference element in the case where this group of pixels is the image of a reference element.

Here, the brightness of the pixels located in two adjacent faces has a predetermined difference and the brightness of the pixels located in two diagonally opposite faces of the calibration element are similar. The fourth intermediate ratings awarded to the pair are therefore determined accordingly.

The pairs of two groups of pixels for which the difference between a distance measured between these two groups and a reference distance, and/or an angle measured between the straight line passing through these two groups and a reference direction and a reference angle, and/or the brightness measured in the vicinity of these two groups and a reference brightness and/or the brightness difference between two predetermined relative position points in relation to each group of pixels and a reference brightness difference is greater than a threshold value can also be excluded from the selection made in step l);

In the case of the angle of inclination, this amounts to considering that the inclination of the user's head is limited to a determined range of angles and to eliminating the pairs of groups of pixels for which the angle measured between the straight line passing through these two groups and a direction representing, for example, the image of a horizontal straight line indicates that the user's head is not in a natural posture.

For example, the pairs which would indicate that the head 10 of the user is inclined at an angle greater than 20 degrees around the horizontal axis AH of the user's head are eliminated.

The global rating of each pair is, for example, obtained by multiplying all of the intermediate ratings awarded to this pair.

Alternatively, these intermediate ratings can be weighted according to the importance or reliability of the criterion considered.

Said intermediate ratings can also be awarded according to other methods, for example by awarding an identical rating to all the pairs of which the characteristics described above are located in an interval of predetermined values.

The intermediate ratings can also be calculated in such a way as to have an exponential increase according to the reduction in the difference between the measured characteristics of the pair and the corresponding reference values.

The pair of groups of pixels having the best global rating is identified with the looked-for pair of images of the calibration elements.

In the case where this determination of the positions of the images of the calibration elements is carried out on a resampled image, it can be envisaged to repeat on the non-resampled image the step of convolution by a detection matrix reproducing the expected image brightness distribution of the calibration element, in a reduced zone of the non-resampled image centered around the position of the non-resampled image corresponding to each position determined for the calibration elements on the resampled image (block 700 in FIG. 1).

The size of the detection matrix used in this step is then adapted to the non-resampled image.

Step d)

A measured value of the brightness (block 800 in FIG. 1), luminance or chrominance is determined according to the type of calibration element used, of at least one part of the image of this brightness calibration element or of at least one part of the image located close to this brightness calibration element.

The part of the image of the brightness calibration element for which a measured brightness value is determined is referred to below as the measurement zone. It straddles, for example, said two contrasted zones of the calibration element.

The measured brightness value is a mean value over the entire measurement zone.

Here, this measurement is carried out in a zone straddling the four contrasted zones, preferably centered on the center of the calibration element, which corresponds to the maximum brightness pixel.

Here, the brightness measurement zone has a square shape and a size less than the dimensions of the image of the calibration element. The use of a measurement zone having these characteristics makes the determined mean barely prone to an error in the centering of this measurement zone in relation to the center of the calibration element.

Alternatively, a measured value of the brightness of each part of the image of this brightness calibration element is determined and the mean of these two values is calculated.

Step e)

A parameter for adjusting the optical image-acquisition conditions of said image capture device is modified as a function of this measured value in such a way as to improve the contrast of the image of the contrasted zones ZS, ZC of the calibration element 21D, 21G, 22H, 22B, 23, 24.

More precisely, in step e), a brightness test is carried out (block 300 in FIG. 1):

the difference between the measured value of the brightness determined in step d) and a target brightness value is determined, this difference is compared with a predetermined maximum value of this difference, according to this comparison, the parameter for adjusting the optical acquisition conditions of the image capture device is modified in such a way as to make said measured value extend toward said target brightness value.

The target brightness value is predetermined by a prior calibration step. It may, for example, be determined on the basis of a first image captured under optimum brightness conditions, or it may be determined on the basis of a mean value of a measured value of the brightness on usable images.

In practice, if this difference is greater than a predetermined maximum value of this difference, the modification of the parameter for adjusting the optical acquisition conditions (block 310 in FIG. 1) of the image capture device in step e) is, for example, equal to the difference between the target brightness value and said measured brightness value divided by said predetermined maximum value of the difference between this target brightness value and this measured value.

If this difference is less than a predetermined maximum value of this difference, the modification of the adjustment parameter is zero and the method moves on directly to step g) (block 900 in FIG. 1).

Said predetermined maximum value of the difference between the target value and the measured brightness value depends, for example, on the number of steps of adjustment of the parameter for adjusting the optical acquisition conditions of the image capture device. The more this adjustment parameter comprises a large number of adjustment steps, the greater the predetermined maximum value of the difference will be in order to nevertheless allow a fast adjustment of this parameter.

Ideally, the modification of the adjustment parameter depends on the measured brightness value, the target value and the current value of the adjustment parameter.

The link between brightness and the adjustment parameter is not necessarily linear on the cameras. For example, a small modification of the adjustment parameter when the image is saturated or underexposed may remain without visible effect.

Thus, it may be advantageous to vary the predetermined maximum value of the difference according to the current value of the adjustment parameter. The parameter for adjusting the optical acquisition conditions of the image capture device is an aperture and/or a gain and/or an exposure time parameter.

In practice, the image capture device is, for example, a video camera in interlaced PAL format. The initial size of the image, before resampling, is, for example, 720×576 pixels.

The "bright" parameter of the camera is then adjusted.

The "bright" parameter is not a physical parameter of the camera, but an instruction. The camera is, for example, used in semiautomatic adjustment mode. According to the requested "bright" parameter, the camera then automatically adjusts the following three hardware parameters:
iris or aperture or diaphragm,
gain,
pause or shutter time Step f)

Another image with the modified parameter for adjusting the optical acquisition conditions is captured (block 100 in FIG. 1).

Step g)

Said looked-for geometric/physiognomic mounting parameter is determined on the basis of this other image (block 900 in FIG. 1).

To do this, at least one geometric characteristic of the reference element of the accessory is identified on the image captured in step f).

Here, a geometric characteristic of the brightness calibration element is identified.

To determine, for example, the interpupillary distance, it suffices to measure the distance separating the pupils on the image captured in step f), then to determine a scale factor.

This scale factor is, for example, determined by comparing the length of the calibration element on the image and its real length.

The scale factor is then applied to the interpupillary distance measured on the image in order to determine the real interpupillary distance of the user.

After step e), steps b) to e) are preferably repeated while the brightness value measured in step d) is outside an interval of predetermined values, and steps f) and g) are carried out when this measured value is inside said predetermined interval.

Thus, the brightness of the image used to determine the geometric/physiognomic parameter is optimal.

Alternatively, it can be provided, before step b), to implement a first rough and fast adjustment of the acquisition parameters of the image capture device, by the following steps, shown on blocks 100', 200 and 300' in FIG. 1:

pa) capturing a preliminary image of the user's head, pb) determining a measured value of the mean brightness of at least one reduced zone of this preliminary image, this reduced zone being suitable for covering at least one part of the image of the users head, pc) roughly adjusting the parameter for adjusting the optical acquisition conditions of the image capture device according to this measured value in such a way as to improve the contrast of the captured image of the user's head, pd) using the parameter for adjusting the optical acquisition conditions obtained in step pc) to adjust the optical conditions of the image capture of step b).

The reduced zone of the image captured in step pa) used in step pb) is, for example, a central zone 12 (FIG. 2) of the image 11, the dimensions of which are equal to half of the dimensions of the total image. This central zone generally comprises the user's eyes when the image is captured from the front.

Alternatively, if the captured image is a profile image of the user, it can be envisaged that the reduced zone used in step pb) is a left or right half of the image.

A mean luminance or chrominance of this reduced zone of the image is therefore determined in step pb).

More particularly, step pc) consists in:
determining the difference between the measured value determined in step pb) and a target brightness value,
comparing this difference with a predetermined maximum value of this difference, and
according to this comparison, in step pc), adjusting the parameter for adjusting the optical acquisition conditions of the image capture device in such a way as to make said measured value extend toward said target brightness value.

As in the previously described step e), the target brightness value is predetermined by a prior calibration step.

In practice, as in step e), the modification of the parameter for adjusting the optical acquisition conditions of the image capture device in step pc) is, for example, equal to the difference between the target brightness value and said measured brightness value divided by said predetermined maximum value of the difference between this target brightness value and this measured value.

Said predetermined maximum value of the difference between the target value and the measured brightness value depends, for example, on the number of steps of adjustment of the parameter for adjusting the optical acquisition conditions of the image capture device. The more this adjustment parameter comprises a large number of adjustment steps, the greater the predetermined maximum value of the difference will be in order to nevertheless allow a fast adjustment of this parameter.

Ideally, the modification of the adjustment parameter depends on the measured brightness value, the target value and the current value of the adjustment parameter.

It can also be provided that steps pa) to pd) are repeated while the mean brightness value measured on the reduced zone of the image considered is not within an interval of predetermined brightness values.

It will thus be possible to carry out the more precise adjustment of the brightness of the calibration elements more quickly.

It can also be envisaged to repeat this step if the brightness changes abruptly during the acquisition of a series of images.

The present invention is in no way limited to the embodiments described and shown, but the person skilled in the art will be able to produce any variant in keeping with its intent.

An example has been described in which the brightness of the calibration element is determined on a measurement zone straddling the contrasted zones of this calibration element.

It would also be possible to work separately on the light and dark zones of the calibration element, by having two target brightness values and two maximum values of the difference between the measured value and the target value.

As previously mentioned, it is also possible to envisage working with color test patterns. In this case, it would be possible to work on different color channels, and therefore to carry out a processing similar to that in luminance on each channel.

In practice, it would be preferable to choose red and green rather than blue calibration elements since CCD camera sensors are barely sensitive to them.

Finally, it can be envisaged that the brightness measurement carried out triggers the activation of an additional illumination means, for example having electroluminescent diodes, disposed close to the image capture device, in order to modify the illumination conditions during the following image capture.

The invention claimed is:

1. A method for determining at least one geometric/physiognomic parameter associated with the mounting of an ophthalmic lens in a spectacle frame worn by a user, comprising the following steps:
   a) placing an accessory on the user's head, said accessory comprising at least one brightness calibration element, said brightness calibration element including at least two contrasted zones;
   b) capturing an image of the user's head on which said accessory has been placed, using an image capture device;
   c) determining the position of the image of the brightness calibration element of said accessory on said image captured in step b);
   d) determining a measured value of the brightness of at least one part of the image of this brightness calibration element;
   e) modifying a parameter for adjusting the optical image-acquisition conditions of said image capture device as a function of this measured value in such a way as to improve the contrast of the image of the contrasted zones of the calibration element;
   f) capturing another image with the modified parameter for adjusting the optical acquisition conditions; and
   g) determining said looked-for geometric/physiognomic mounting parameter on the basis of this other image.

2. The method as claimed in claim 1, according to which, after step e), steps b) to e) are repeated while the brightness value measured in step d) is outside an interval of predetermined values, and steps f) and g) are carried out when this measured value is located inside said predetermined interval.

3. The method as claimed in claim 1, according to which, the accessory furthermore comprising a reference element having at least one known geometric characteristic, in step g), at least one geometric characteristic of this reference element of the accessory is identified on the image captured in step f).

4. The method as claimed in claim 3, according to which said reference element is combined with said brightness calibration element.

5. The method as claimed in claim 1, according to which, in step d), the part of the image of the brightness calibration element for which a measured value of the brightness is determined straddles said two contrasted zones.

6. The method as claimed in claim 1, according to which, in step d), a measured value of the brightness of each contrasted zone of the image of this brightness calibration element is determined and the average of these determined values is calculated.

7. The method as claimed in claim 1, according to which, in step e),
   the difference between the measured brightness value determined in step d) and a target brightness value is determined,
   this difference is compared with a predetermined maximum value of this difference,
   according to this comparison, the parameter for adjusting the optical acquisition conditions of the image capture device is modified in such a way as to make said measured value extend towards said target brightness value.

8. The method as claimed in claim 1, comprising the following steps, which are preliminary to step b):
   pa) capturing a preliminary image of the user's head,
   pb) determining a measured value of the mean brightness of at least one reduced zone of this preliminary image, this reduced zone being suitable for covering at least a part of the image of the user's head,
   pc) roughly adjusting the parameter for adjusting the optical acquisition conditions of the image capture device according to this measured value in such a way as to improve the contrast of the captured image of the user's head,
   pd) using the parameter for adjusting the optical acquisition conditions obtained in step pc) to adjust the optical conditions of the image capture of step b).

9. The method as claimed in claim 8, according to which, in step pc),
   the difference between the measured value of the brightness determined in step pb) and a target brightness value is determined,
   this difference is compared with a predetermined maximum value of this difference,
   according to this comparison, in step pc), the parameter for adjusting the optical acquisition conditions of the image capture device is adjusted in such a way as to make said measured value extend towards said target brightness value.

10. The method as claimed in claim 1, comprising, in step c), a step k) of detection of the groups of pixels having an isolated brightness peak smaller in size than the brightness calibration element in all directions.

11. The method as claimed in claim 10, according to which a step l) of selection of at least two groups of pixels having an isolated brightness peak detected in step k) is provided, having the highest probability of being associated with the image of two of the brightness calibration elements of the accessory, i.e. at least two groups of pixels for which the difference between

- a distance measured between these two groups and a reference distance, and/or
- an angle measured between the straight line passing through these two groups and a reference direction and a reference angle, and/or
- the brightness measured in the vicinity of these two groups and a reference brightness, and/or
- the brightness difference between two points of predetermined relative positions in relation to each group of pixels and a reference brightness difference is reduced.

12. The method as claimed in claim 1, according to which said contrasted zones of the brightness calibration element comprise a dark gray zone and a light gray zone.

13. The method as claimed in claim 1, according to which each brightness calibration element comprises four alternating contrasted zones, each zone forming a right angle with a common apex with the right angles formed by the other zones.

14. A method for determining at least one geometric/physiognomic parameter associated with the mounting of an ophthalmic lens in a spectacle frame worn by a user, comprising the following steps:

a) placing an accessory on the spectacle frame, the spectacle frame being located on the user's head, said accessory comprising at least one brightness calibration element, said brightness calibration element including at least two contrasted zones;

b) capturing an image of the user's head on which said accessory has been placed, using an image capture device;

c) determining the position of the image of the brightness calibration element of said accessory on said image captured in step b);

d) determining a measured value of the brightness of at least one part of the image of this brightness calibration element;

e) modifying a parameter for adjusting the optical image-acquisition conditions of said image capture device as a function of this measured value in such a way as to improve the contrast of the image of the contrasted zones of the calibration element;

f) capturing another image with the modified parameter for adjusting the optical acquisition conditions; and g) determining said looked-for geometric/physiognomic mounting parameter on the basis of this other image.

15. The method as claimed in claim 14, according to which, after step e), steps b) to e) are repeated while the brightness value measured in step d) is outside an interval of predetermined values, and steps f) and g) are carried out when this measured value is located inside said predetermined interval.

16. The method as claimed in claim 14, according to which, the accessory furthermore comprising a reference element having at least one known geometric characteristic, in step g), at least one geometric characteristic of this reference element of the accessory is identified on the image captured in step f).

17. The method as claimed in claim 16, according to which said reference element is combined with said brightness calibration element.

18. The method as claimed in claim 14, according to which, in step d), the part of the image of the brightness calibration element for which a measured value of the brightness is determined straddles said two contrasted zones.

\* \* \* \* \*

UNITED STATES PATENT AND TRADEMARK OFFICE
CERTIFICATE OF CORRECTION

| | | |
|---|---|---|
| PATENT NO. | : 9,116,365 B2 | |
| APPLICATION NO. | : 13/985170 | |
| DATED | : August 25, 2015 | |
| INVENTOR(S) | : Ahmed Haddadi | |

It is certified that error appears in the above-identified patent and that said Letters Patent is hereby corrected as shown below:

In the Specification:

Column 16, line 29, cancel the text beginning with "The reduced zone of" to and ending "from the front" in column 16, line 34, and insert the following paragraph:

--The reduced zone of the image captured in step pa) used in step pb) is, for example, a central zone I2 (FIG. 2) of the image I1, the dimensions of which are equal to half of the dimensions of the total image. This central zone generally comprises the user's eyes when the image is captured from the front.--

Signed and Sealed this
Sixteenth Day of August, 2016

Michelle K. Lee
*Director of the United States Patent and Trademark Office*